United States Patent
Kana et al.

(10) Patent No.: US 8,597,353 B2
(45) Date of Patent: Dec. 3, 2013

(54) INTERBODY FUSION DEVICE AND ASSOCIATED METHODS

(75) Inventors: Richard J. Kana, Lexington, TX (US); Brian Burkinshaw, Pflugerville, TX (US); John Rossman, Austin, TX (US); Kevin Dunworth, Dripping Springs, TX (US)

(73) Assignee: SpineSmith Partners, L.P., Austin, TX (US)

(*) Notice: Subject to any disclaimer, the term of this patent is extended or adjusted under 35 U.S.C. 154(b) by 0 days.

(21) Appl. No.: 13/200,911

(22) Filed: Oct. 4, 2011

(65) Prior Publication Data

US 2012/0277867 A1     Nov. 1, 2012

Related U.S. Application Data

(63) Continuation-in-part of application No. 11/759,219, filed on Jun. 6, 2007, now Pat. No. 8,273,127, and a continuation-in-part of application No. 12/018,703, filed on Jan. 23, 2008, and a continuation-in-part of application No. 12/044,186, filed on Mar. 7, 2008.

(60) Provisional application No. 61/404,468, filed on Oct. 4, 2010, provisional application No. 60/981,414, filed on Oct. 19, 2007, provisional application No. 60/981,358, filed on Oct. 19, 2007.

(51) Int. Cl.
    *A61F 2/44*         (2006.01)

(52) U.S. Cl.
    USPC ........................... 623/17.11; 606/246

(58) Field of Classification Search
    USPC ................ 606/246–249, 90, 105; 623/17.11–17.16; 411/412
    See application file for complete search history.

(56) References Cited

U.S. PATENT DOCUMENTS

| | | | |
|---|---|---|---|
| 3,426,642 A * | 2/1969 | Phipard, Jr. ................ 411/417 |
| 4,599,086 A * | 7/1986 | Doty ........................... 606/86 A |
| 4,977,764 A | 12/1990 | Runnalls ........................ 70/63 |
| 6,066,175 A * | 5/2000 | Henderson et al. ......... 623/17.11 |
| 2005/0049590 A1 | 3/2005 | Alleyne et al. ................ 606/61 |
| 2006/0074488 A1 | 4/2006 | Abdou ...................... 623/17.11 |
| 2006/0241621 A1 | 10/2006 | Moskowitz et al. ........... 606/72 |
| 2007/0162028 A1 | 7/2007 | Jackson et al. ................ 606/73 |

OTHER PUBLICATIONS

International Patent Application No. PCT/US2011/001716, "*International Search Report dated Jan. 13, 2012*," International Filing Date Oct. 4, 2011.

* cited by examiner

*Primary Examiner* — Mary Hoffman
*Assistant Examiner* — Tara Carter
(74) *Attorney, Agent, or Firm* — Winstead PC

(57) ABSTRACT

A medical device comprising a non-enclosed housing configured to fit between two adjacent vertebrae; one or more housing fasteners extending at least partially through the housing, one or more driving mechanisms operationally positioned in relationship to at least one housing fastener, such that activation of at least one driving mechanism engages and drives at least one housing fastener to compress into at least one adjacent vertebrae and one or more plates removably coupled to the housing.

15 Claims, 6 Drawing Sheets

SECTION G-G

SECTION E-E

INTERBODY FUSION DEVICE AND ASSOCIATED METHODS

CROSS REFERENCE TO RELATED APPLICATIONS

This application claims priority to U.S. provisional application 61/404,468, filed Oct. 4, 2010, and is a continuation-in-part of U.S. patent application Ser. No. 11/759,219, filed Jun. 6, 2007 now U.S. Pat. No. 8,273,127, and is a continuation-in-part of co-pending U.S. patent application Ser. No. 12/018,703, filed Jan. 23, 2008, which claims priority to U.S. Provisional Application No. 60/981,414, filed Oct. 19, 2007, and is a continuation-in-part of co-pending U.S. patent application Ser. No. 12/044,186, filed Mar. 7, 2008, which claims priority to U.S. Provisional Application No. 60/981,358, filed Oct. 19, 2007, all of which are incorporated herein by reference in their entirety.

FIELD OF THE INVENTION

The invention herein relates generally to the field of spinal fusion. In particular, this invention is drawn to spinal fusion devices and associated methods and is particularly applicable to cervical fusion.

BACKGROUND OF THE INVENTION

The spine can be considered to be a series of movable segments made up of vertebrae and discs. Due to trauma, disease, and/or aging, the spine may be subject to degeneration. This degeneration may destabilize the spine and cause pain and/or nerve damage. Medical procedures are often required to either ease back pain, repair damage, or to prevent future damage.

One procedure that is often used to treat back or neck pain or other spinal damage is spinal fusion. Spinal fusion is a surgical technique used to combine two or more adjacent vertebrae. Supplemental bone tissue or a synthetic substitute is used in conjunction with the patient's natural osteoblastic processes in a spinal fusion procedure. Spinal fusion is used primarily to eliminate back pain caused by the motion of the damaged vertebrae by immobilizing the damaged vertebra through fusion with the adjacent vertebrae. Conditions for which spinal fusion might be done include degenerative disc disease, treatment of a spinal tumor, a vertebral fracture, scoliosis, degeneration of the disc, spondylolisthesis, or any other condition that causes instability of the spine.

One problem with typical prior art fusion techniques is that fusion devices, or associated plates or fasteners, may protrude from the spine, or work themselves loose and back out of or away from the bone causing discomfort, damage, soft tissue erosion or danger to surrounding vascular or neurological tissues. Another problem with spinal fusion techniques relates to device migration or subsidence. For example, prior to formation of a bone fusion, a vertebral endplate may fracture, or an underlying or pre-existing Schmorls Node may result in a weakened vertebral body causing device migration from the desired position or collapse of the intended fusion space. In examples where bone screws are used, inadequate fixation of the bone screws into the vertebral bodies may allow device migration as the bone resorbs or remodels. In yet another example, poor selection or preparation of bone tissue or a synthetic bone substitute used to fill the inner body space of the interbody fusion device results in a poor, weak or non-fusion. Still other issues such as poor endplate preparation and unstable surfaces; failure of the surgeon to provide adequate blood flow or blood transfer to the graft site via endplate perforation, may result in a failure to fuse bone. Yet other problems associated with poor surgical technique; anatomic obstructions, such as bony structures, delicate arterial structures or other soft tissues; inadequate instrumentation or a combination of these may contribute to a poor outcome.

There is therefore a need for spinal fusion devices and related spinal fusion procedures that adequately addresses degenerative disc disease and other spinal conditions, while providing improvements over the prior art.

SUMMARY OF THE INVENTION

This invention provides a solution to the problems and disadvantages described above by providing designs specifically developed to address many of the issues described previously. Specifically, the invention is directed to a spinal fusion device intended to improve the surgical technique of the surgeon, allow better visibility and access to the vertebral endplate sight for endplate preparation and graft material insertion; simplify the overall procedure in general; and improve blood flow and blood transfer to the graft material within the interbody fusion device. More specifically, the invention is a medical device comprising a non-enclosed housing configured to fit between two adjacent vertebrae; and one or more plates removably couplable to the open face of the non-enclosed housing, and further comprising multiple fastener types, with one or more (housing) fasteners extending at least partially through the housing, and optionally, one or more other fasteners being capable of protruding through the removably couplable plates into the superior or inferior adjacent vertebrae, wherein any or all of the fasteners from the group may be cannulated or fenestrated (creating a perforated structure). In this regard, the fasteners are configured to allow fluids to flow through the fastener, through one or more openings in the housing/cage, and into the space defined by the device and two vertebrae. The fasteners can thus have transverse holes and a hollow bore, or can have slots to permit fluid flow. Similarly, the cage can include drainage hole or drainage slots. Even more specifically, the invention is designed to be especially suited for cervical vertebral fusion procedures, but may have equal benefit for lumbar or thoracic fusion applications.

In one broad respect, this invention is a medical device comprising a non-enclosed housing configured to fit between two adjacent vertebrae; and one or more plates removably coupled to the housing. The medical device further comprising one or more housing fasteners extending at least partially through the housing, wherein at least one housing fastener selected from the group having a cannulation and/or fenestration therethrough.

In another broad respect, this medical device may further comprise one or more driving mechanisms operationally positioned in relationship to at least one housing fastener, such that activation of at least one driving mechanism engages and drives at least one housing fastener to compress into at least one adjacent vertebrae.

In still another broad respect, the cannulated and, or fenestrated fasteners would allow blood and, or marrow from the adjacent vertebrae to flow through the cannulations and/or fenestrations, through drainage ports within the housing and into the inner space of the interbody fusion device to augment the supplemental bone tissue or a synthetic bone substitute used in conjunction with the patient's natural osteoblastic processes in a spinal fusion procedure.

In yet another embodiment, the medical device further comprising two or more locking fasteners, each extending at least partially through at least one removably coupled plate; and a locking mechanism operationally positioned in relationship to the locking fasteners such that activation of the locking mechanism engages and drives the locking fasteners to lock together the at least one plate and the housing, and enclosing the open face of the non-enclosed housing.

In still another embodiment, the medical device further comprises an embodiment with a non-enclosed opening of the housing configured with an anterio-laterally offset opening to provide easier access to the interior space of the housing and vertebral endplates, thus minimizing the need to retract or remove anatomic obstructions, such as bony structures, delicate arterial structures or other soft tissues during preparation of the endplates or insertion of the supplemental bone tissue or a synthetic bone substitute used in conjunction with the patient's natural osteoblastic processes in a spinal fusion procedure. This anterio-lateral offset opening minimizes destruction or damage to those tissues and allows for more minimally invasive surgical techniques, simpler surgical technique and faster patient recovery. The anterio-lateral offset is ideally between 5° and 30° from midline of the body, and more specifically between 10° and 25° from midline of the body, and even more specifically between 15° and 20° from midline of the body. This may be particularly important in cervical procedures, where minimization of the need to retract the trachea for visualization and access to the cervical disc is highly desired. However, it should be appreciated by one skilled in the art that these features may be equally important for alternative approaches applied to the thoracic or lumbar vertebral procedures.

In another broad respect this is a process for making an implant which comprises forming a medical device comprising: a non-enclosed housing configured to fit between two adjacent vertebrae; and one or more plates removably coupled to the housing.

DETAILED DESCRIPTION

Figure 1A:
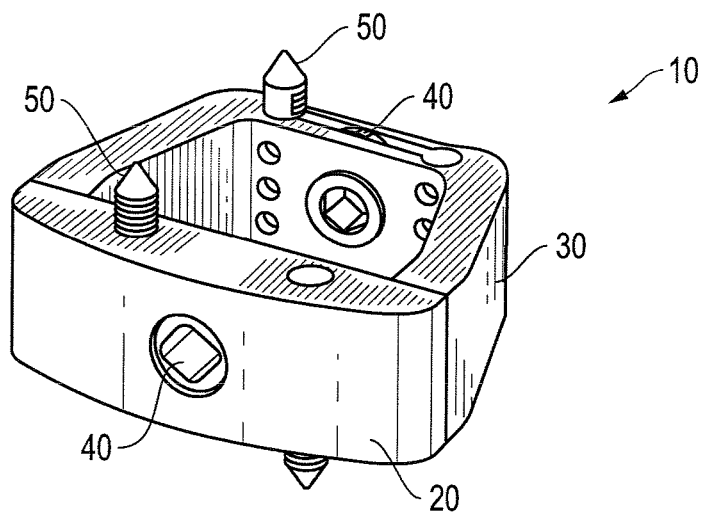
FIG. 1 illustrates a device of this invention having a gear mechanism 40 in both the face plate 20 and housing (cage) 30 that each can be actuated to drive pins 50 into a vertebral body.
Figure 1B:
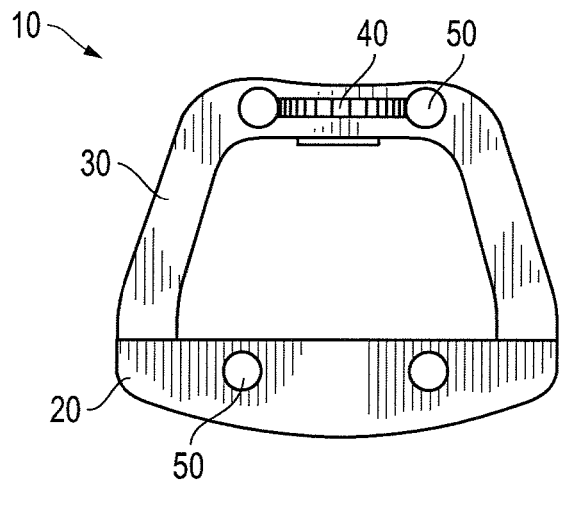
Figure 1C:
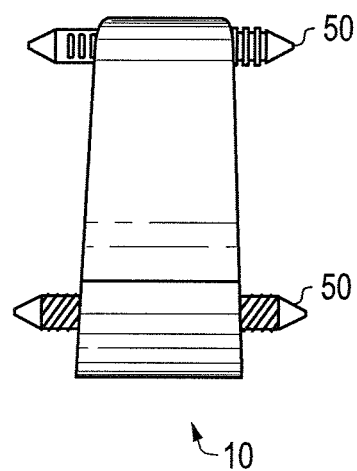
Figure 1D:
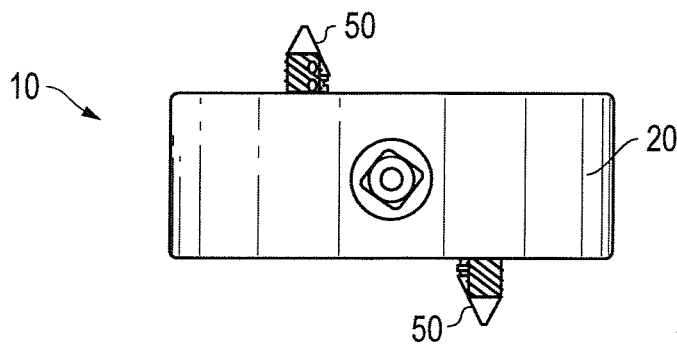

The specific features, aspects, and advantages of the present invention will become better understood with regard to the following description, appended claims, and accompanying drawings where:

FIG. 1 illustrates several image perspectives depicting a possible version of the device 10 having a straight gear driving mechanism 40 in both the removably coupled faceplate 20 and the posterior aspect of a non-enclosed, horseshoe-shaped housing 30; the driving mechanism(s) 40, (i.e.: gears) would be activated by a driver such as a screw driver, torx wrench, hex wrench or similar device, which in turn, engages the rack-and-pinion style fixation pins 50 embedded alongside the driving mechanism 40 and causes the pins 50 to be driven or embedded into the vertebral endplates, above and below the device. It should be noted that the driving mechanisms 40 in both the removably coupled faceplate 20 and the posterior aspect of a non-enclosed, horseshoe-shaped housing 30 could be engaged independently or simultaneously by the clinician.

Figure 2:
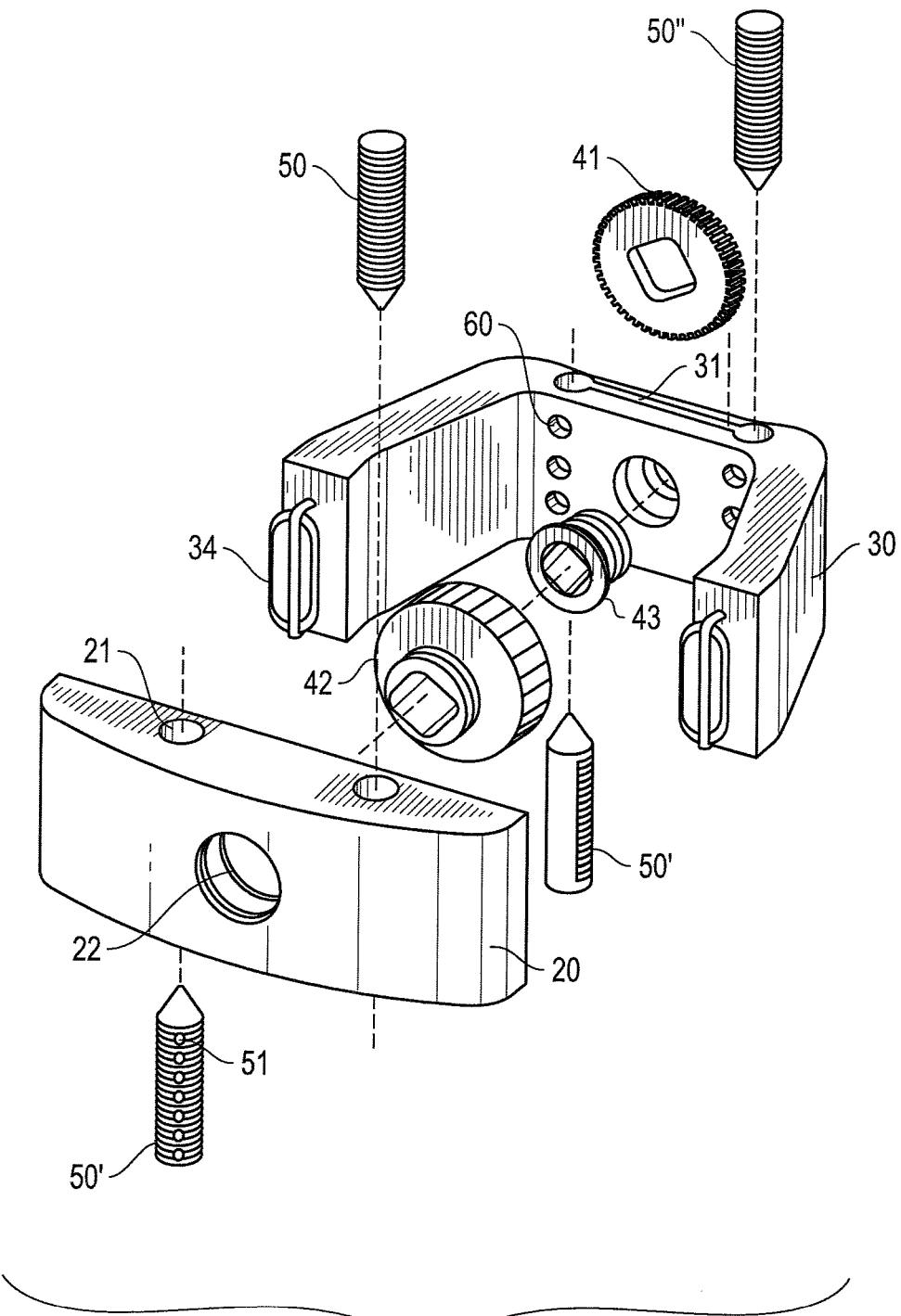
FIG. 2 shows an exploded view of the device of FIG. 1.

FIG. 2 illustrates a line and shaded exploded image in isometric perspective. depicting various movable fixation pins 50 and mechanisms 40 for deploying them. Pin 50' depicts a straight set of teeth and correlate with gear 41, functioning similarly to a rack-and-pinion mechanism. The mechanism would provide a straight linear motion of the pin. Pin 50" is a variation where the teeth wrap around the entire pin diameter, but functions in the same manner. These teeth may provide additional gripping in the vertebral body. Gear 41 depicts a bushing 43 with a (hexagonal) driver interface. The bushing 43 aids in the assembly of the gear to the cage 30 and then facilitates a driver, such as a screwdriver type device. The (hexagonal) driver interface feature may be any popular or custom form of a driver receptacle. Also shown are cannulated and, or fenestrated drainage holes in the pins 51, and corresponding drainage ports 60 in the housing body which open up to the inside of the intervertebral body housing (cage) component 30. The sizes and number of these ports 60 could be variable and made available to facilitate flow, as noted in the description above. These same ports 60 could be available for all pin locations. Protrusions 34 provide structure to fit into voids (not shown) in the face plate 20. The face plate 20 includes one or more bores 21 sized for receipt of the pins 50. The face plate also includes a transverse bore 22 for receiving the inner portion of gear 42. The housing 30 may include a slot suitably fashioned to receive gear 41, which itself receives bushing 43.

Figure 3:
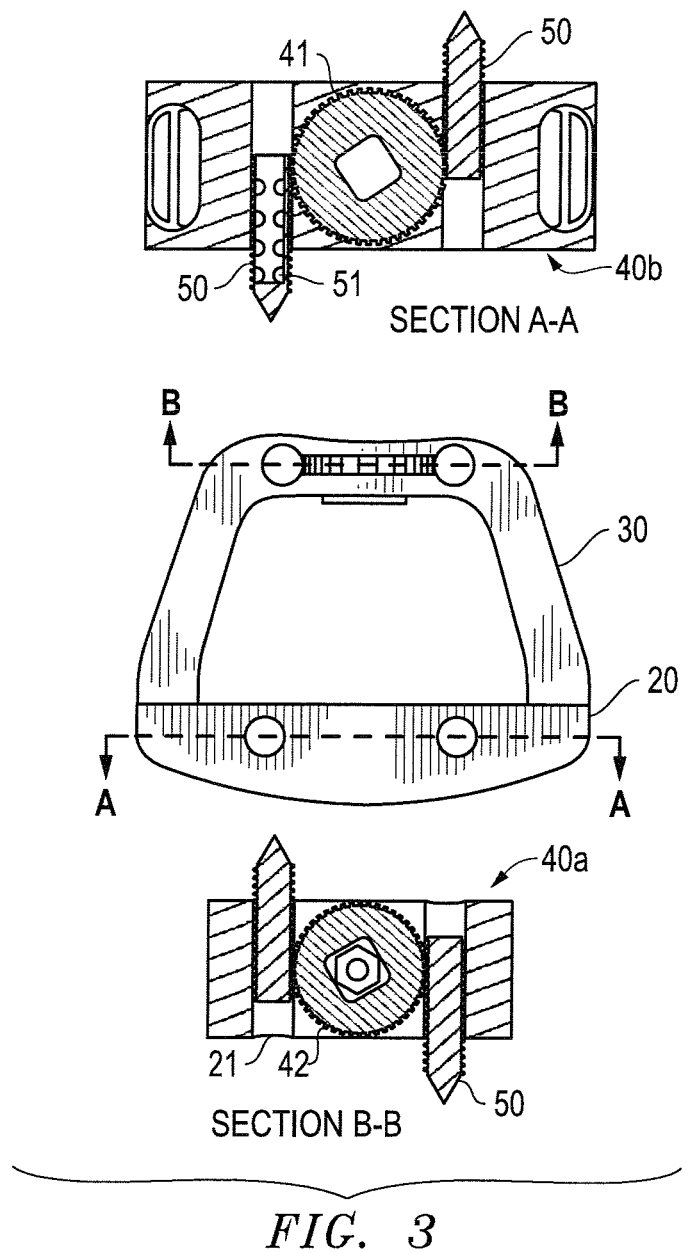
FIG. 3 shows cutaway views of the gear mechanisms 40a and 40b as assembled.

FIG. 3 illustrates a section detail view (section B-B) of a driving (gear) mechanism 40a and two pins 50 taken through the posterior aspect of a non-enclosed, horseshoe-shaped housing 30; while section A-A shows a driving (gear) mechanism 40b and two pins 50 taken through the removably coupled faceplate 20. Also illustrated is a more detailed example in mechanism 40b of a cannulated and fenestrated pin 50 with drainage holes 51 to facilitate blood and, or marrow transfer through the vertebral endplate and ultimately into the intervertebral body housing (cage) component to augment the supplemental bone tissue or a synthetic bone substitute used in conjunction with the patient's natural osteoblastic processes in a spinal fusion procedure.

Figure 4:
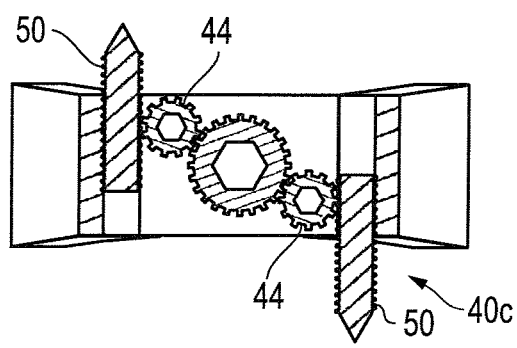
FIG. 4 shows a gear mechanism 40c including additional gears 44.

FIG. 4 illustrates a similar gear mechanism 40c with additional gears 44 are added to the assembly. The additional gears 44 would permit a wider space between the two opposing pins 50 while maintaining a similar overall height of the device. Also, additional gears allow for a different ratio of driver rotations versus that of the pin rotation and/or forward advancement. Additional gears could be used with either the rack-and-pinion mechanism (shown) or a worm gear mechanism.

Figure 5A:
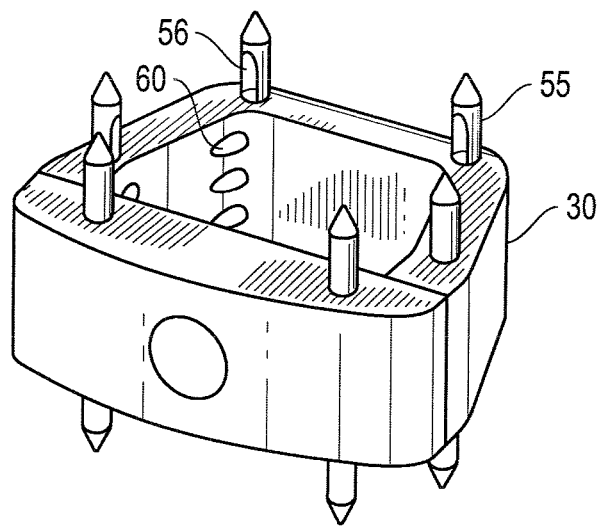
FIGS. 5a and 5b show an implant with fixed pins that contain slots or troughs to allow fluids to flow into the inner void of the device through bores in the faceplate and/or housing.
Figure 5B:
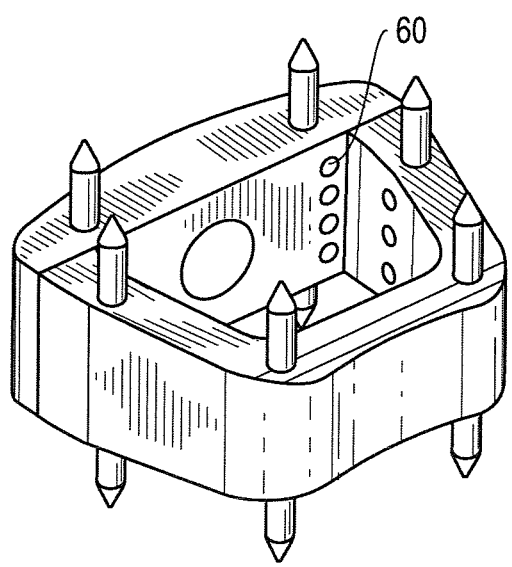

FIGS. 5a and 5b illustrate a device with a version of non-movable (fixed) fixation pins 55, or alternately, pins with limited motion. While this image depicts six (6) fixed pins, more or less could be utilized. The positioning of the pins could easily vary as well. As previously stated, a second option with this pin style is to allow limited motion. The pins could be allowed to self-center themselves between the vertebral bodies, with maximum motion controlled by the height of plate 20 and housing 30. A trough or slot integral to the pin 56 would allow for bone marrow and blood flow from the vertebral bodies to flow into the interior space of the intervertebral (cage) body and penetrate augmented bone chips and/or artificial carriers designed to promote bony fusions through the implant. This same feature could be added to any version of the pins. Drainage ports 60, which open to the inside of the cage component, are also shown in various aspects which cooperate with the slots 56 or other communications of the pins.

Figure 6:
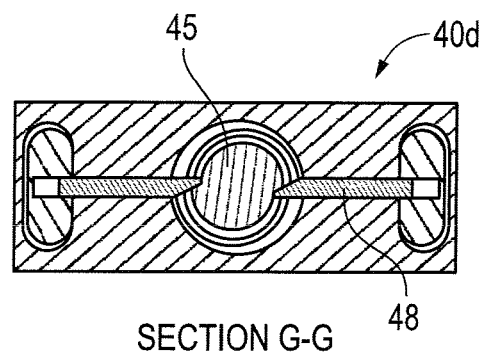
FIG. 6 shows a vault door mechanism 40d that when actuated drives pins to lock the faceplate and housing in place.
Figure 6:
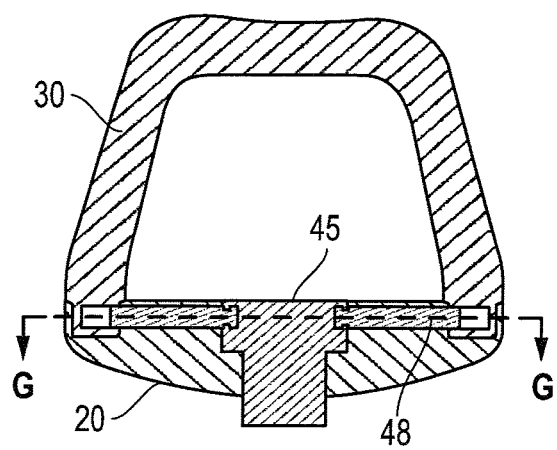

FIG. 6 illustrates several images depicting a typical 2-piece type device, where the cover has an integrated "vault door" type locking mechanism 40d. The designs uses a gear or cam type mechanism 45 that when rotated will simultaneously slide two or more locking pins 48 which effectively cross-pin the faceplate to the intervertebral body (cage) component 30. FIG. 6 depicts the locking pins 48, in cross-sections E-E and G-G, engaged into receiving holes located on the cage component 30. Although not depicted, this same mechanism could be arranged in a way to allow the locking pins to pass into and then through the cage component 30, or they could also protrude from the cage, and at the same time perform as fixation pins.

Figure 7A:
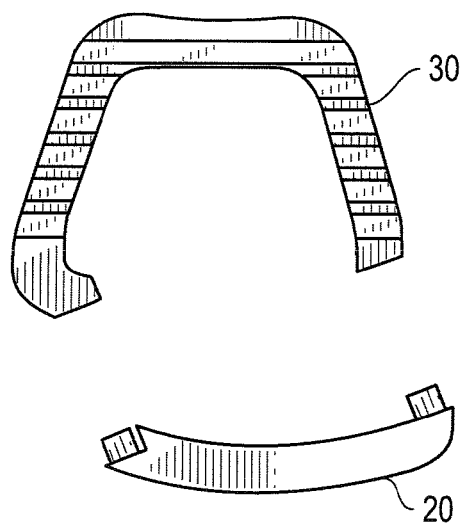
FIGS. 7a and 7b show an implant that includes an offset opening for the faceplate.
Figure 7B:
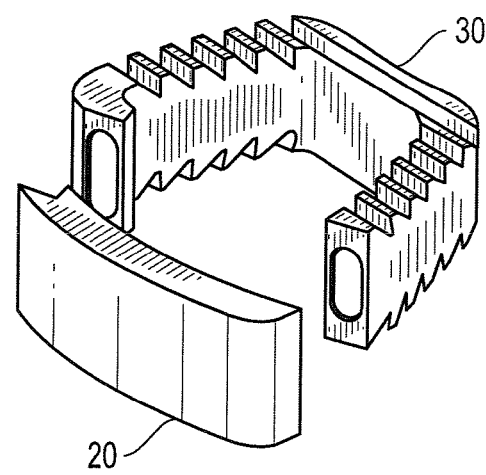

FIGS. 7a and 7b illustrate a 2-piece cervical concept intervertebral body fusion device showing an anterio-lateral offset opening for the faceplate 20, with a suggested offset angle of 20 degrees. However, it should be noted that one skilled in the art would recognize that the concept could be applied equally to both thoracic and lumbar devices, and the that offset angle for the faceplate 20 could easily be varied from 0-90 in anterio-lateral or posterior-lateral orientations, depending on the intended application and approach angle for surgery. Although not shown in these drawings, it should also be understood that one skilled in the art could apply all of the previously described driver mechanisms and fixation pin concepts to this concept with minimal variations in design, if any at all.

Figure 8:
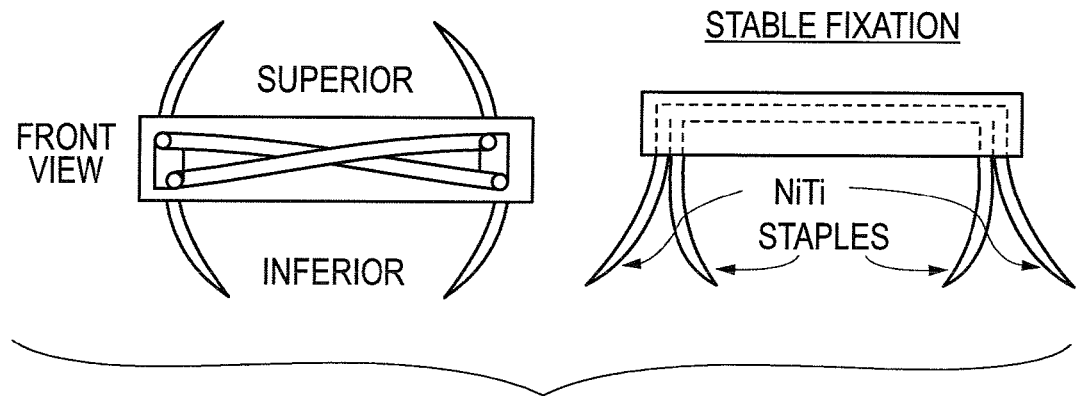
FIG. 8 shows means of fixation for attaching a faceplate to a housing and an endplate of a vertebral body.

FIG. 8 describes and illustrates various possible means of fixation for attaching the faceplate of a device to both the intervertebral body (cage) component and the cephalad (upper) endplate and the caudal (lower) endplate adjacent to the device. In particular, the hand-drawn sketch illustrates the use of NiTi (nitinol) wire or staples in a unique, possibly offset "z"-pattern, that could be utilized to criss-cross the faceplate, penetrate the housing and ultimately penetrate the cephalad and the caudal endplates adjacent to the device to secure fixation. It should be noted that one skilled in the art would recognize that this concept could also be modified by the use of other attachment means to accomplish a similar result.

Although illustrative embodiments have been shown and described, a wide range of modifications, changes, and substitutions are contemplated in the foregoing disclosure and in some instances, some features of the embodiments may be employed without a corresponding use of other features. For example, the device of this invention can a housing (cage), fixed fasteners (pins), moveable fasteners, actuation assemblies to move the moveable fasteners including but not limited to of gear-driven mechanism, a screw-driven mechanism, and a cam-type mechanism including assemblies with single gears and multiple gears, drainage holes in the cage and/or faceplate, drainage slots in the cage and/or faceplate, drainage holes and hollow bore in the fasteners that align with drainage slots or holes in the cage or faceplate, drainage slots in the fasteners that align with drainage holes or slots in the cage or faceplate to permit fluid flow, a removable plate, fasteners with ridges, a cage and factplate with an anterio-lateral offset, ridges on the cage and/or faceplate to help prevent backing-out of the device, and combinations thereof. In one embodiment, fastener refers to fasteners/pins that are adapted such that the fasteners may contact and penetrate vertebrae. Accordingly, it is appropriate that the appended claims be construed broadly and in a manner consistent with the scope of the embodiments disclosed herein.

What is claimed is:

1. A medical device comprising:
a non-enclosed housing configured to fit between two adjacent vertebrae; one or more housing fasteners extending at least partially through the housing, one or more driving mechanisms operationally positioned in relationship to at least one housing fastener, such that activation of at least one driving mechanism engages and drives at least one housing fastener to compress into at least one adjacent vertebrae and one or more plates removably coupled to the housing, and further comprising one or more plate fasteners extending at least partially through at least one plate and further comprising one or more driving mechanisms operationally positioned in relationship to at least one plate fastener such that activation of at least one driving mechanism engages and drives at least one plate fastener to compress at least one adjacent vertebrae to the plate.

2. The medical device of claim 1, wherein at least one housing fastener selected from the group having a cannulation and, or fenestration there through.

3. The medical device of claim 1, wherein at least one housing fastener further comprises a plurality of ridges.

4. The medical device of claim 3, wherein the ridges form a straight line.

5. The medical device of claim 3, wherein each ridge spans the circumference of the housing fastener.

6. The medical device of claim 1, wherein the driving mechanism is selected from the group consisting of gear-driven mechanism, a screw-driven mechanism, or a cam-type mechanism.

7. The medical device of claim 1, wherein at least one plate fastener and, or housing selected from the group is cannulated or fenestrated.

8. The medical device of claim 7, wherein at least one plate fastener further comprises a plurality of ridges.

9. The medical device of claim 8, wherein the ridges form a straight line.

10. The medical device of claim 8, wherein the ridges span the circumference of the one plate fastener.

11. The medical device of claim 1, wherein at least one housing fastener further comprises one or more helical ridges.

12. The medical device of claim 1, wherein the driving mechanism is selected from the group consisting of gear-driven mechanism, a screw-driven mechanism, or a cam-type mechanism.

13. The medical device of claim 1, wherein the housing further comprises one or more drainage ports.

14. The medical device of claim 1, further comprising
two or more locking fasteners, each extending at least partially through the at least one plate; and a locking mechanism operationally positioned in relationship to the locking fasteners such that activation of the locking mechanism engages and drives the locking fasteners to lock together the at least one plate and the housing.

15. The medical device of claim 14, wherein the locking mechanism is selected from the group consisting of a gear-driven mechanism or a cam-type mechanism.

* * * * *